United States Patent [19]

Haslanger et al.

[11] 4,360,685
[45] Nov. 23, 1982

[54] DIOXATRICYCLIC PROSTACYCLIN ANALOGS

[75] Inventors: Martin F. Haslanger, Lambertville; Peter W. Sprague, Pennington, both of N.J.

[73] Assignee: E. R. Squibb & Sons, Inc., Princeton, N.J.

[21] Appl. No.: 305,663

[22] Filed: Sep. 25, 1981

[51] Int. Cl.³ .................. C07D 311/78; C07D 307/93
[52] U.S. Cl. .................................. 549/386; 549/459; 542/426; 424/283; 424/285
[58] Field of Search ............... 260/345.8 R, 345.7 R, 260/346.22, 346.71; 542/426; 549/386, 459

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 R |
| 4,228,180 | 10/1980 | Sprague | 424/285 |
| 4,254,044 | 3/1981 | Sprague | 260/347.8 |

Primary Examiner—Nicky Chan

[57] ABSTRACT

New dioxatricyclic prostacyclin analogs are provided which have the general formula

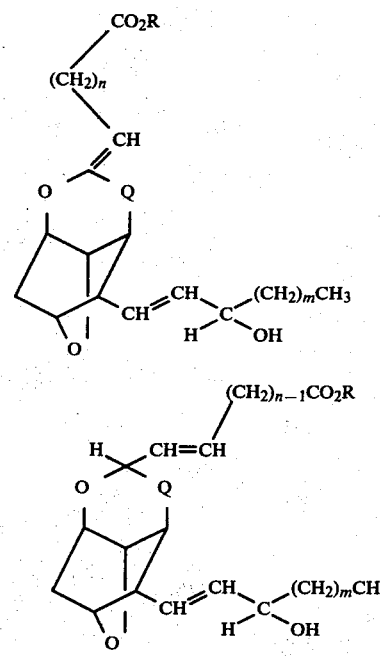

or wherein R is hydrogen or lower alkyl, Q is a single bond or $-CH_2-$, m is 1 to 9 and n is 3 or 4, and all stereoisomers thereof, and are useful as cardiovascular agents.

24 Claims, No Drawings

DIOXATRICYCLIC PROSTACYCLIN ANALOGS

DESCRIPTION OF THE INVENTION

The present invention relates to dioxatricyclic prostacyclin analogs which are cardiovascular agents useful, for example, in the treatment of thrombolytic disease. These compounds have the structural formula

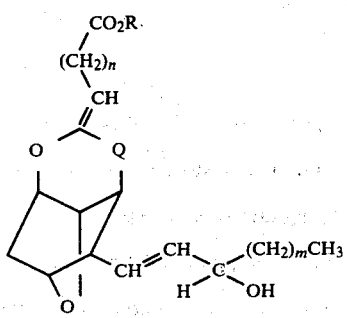

I or

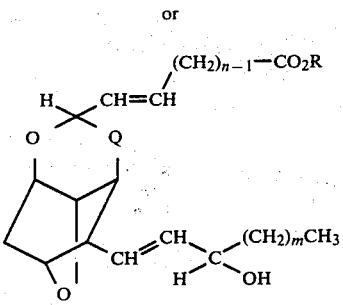

II and including all stereoisomers thereof, wherein R is hydrogen or lower alkyl, Q is a single bond or —$CH_2$—, m is 1 to 9 and preferably 3 to 5, and n is 3 or 4.

The term "lower alkyl" or "alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

Preferred are those compounds of formula I or II wherein R is hydrogen, and m is 4.

The various embodiments of the compounds of the present invention may be represented by the following formulae.

Thus, where Q is —$CH_2$—, the compounds of the invention include:

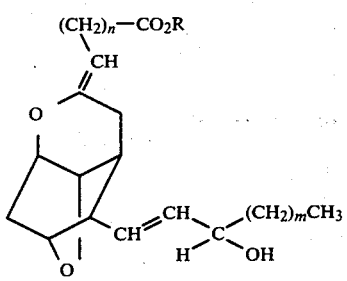

IIIA or

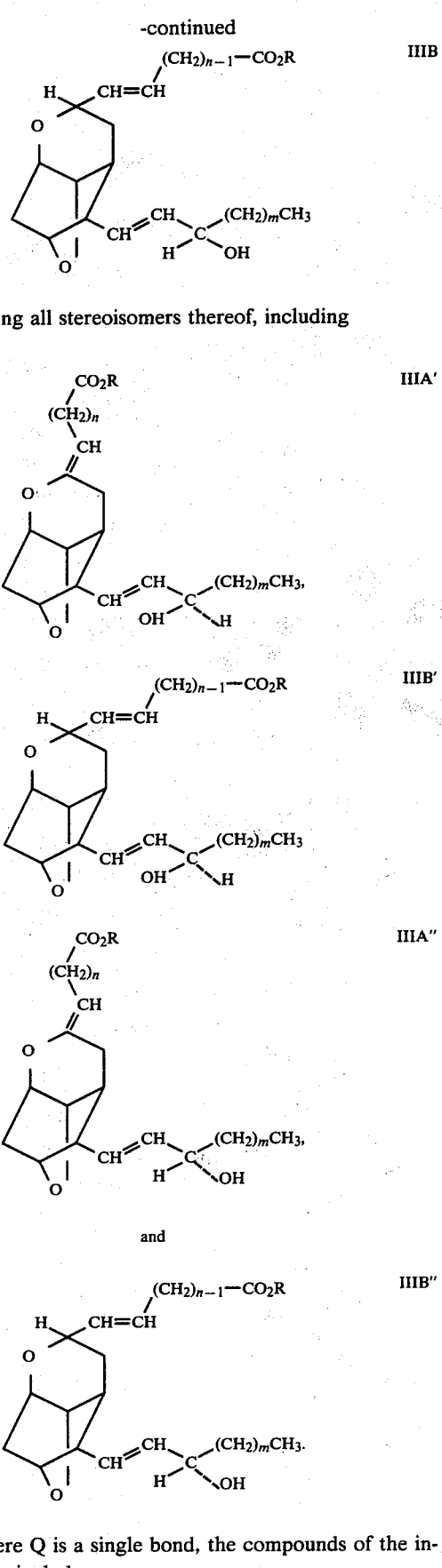

including all stereoisomers thereof, including

Where Q is a single bond, the compounds of the invention include

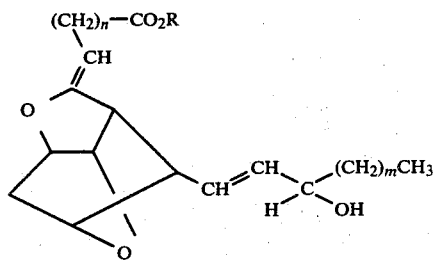

or

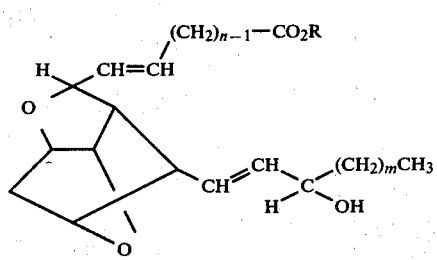

and including all stereoisomers thereof, including

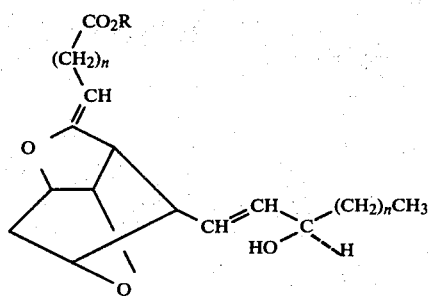

or

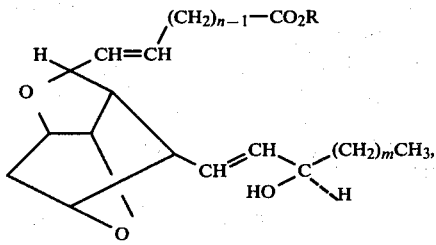

and

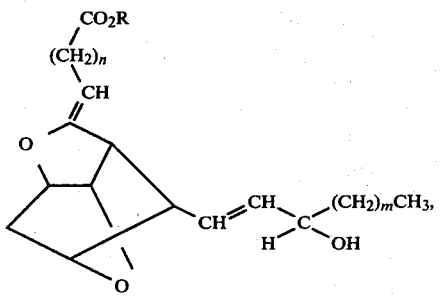

IVA

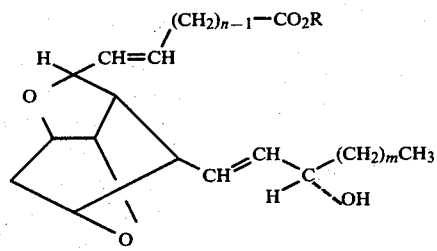

IVB″

The compounds of formula I of the invention may be prepared by a number of steps generally represented by the following reaction sequences.

Where Q in the compound of the invention is a single bond, the following reaction sequence is applicable:

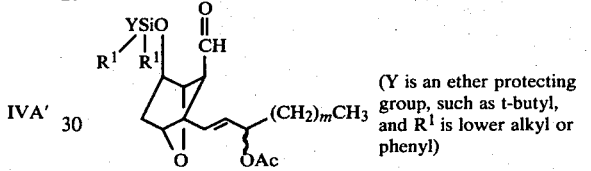

(Y is an ether protecting group, such as t-butyl, and $R^1$ is lower alkyl or phenyl)

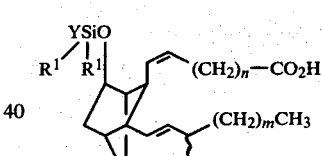

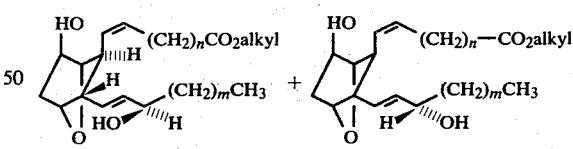

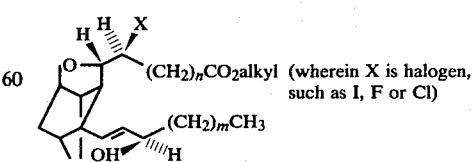  (wherein X is halogen, such as I, F or Cl)

VIIIA

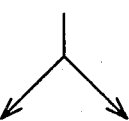

-continued

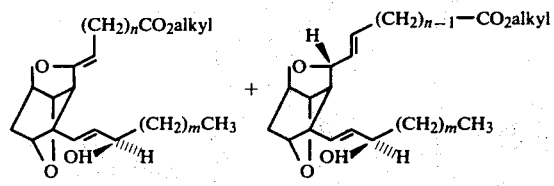

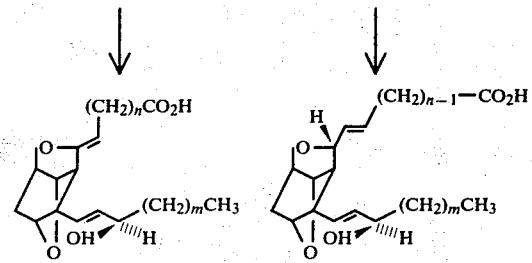

VIIB

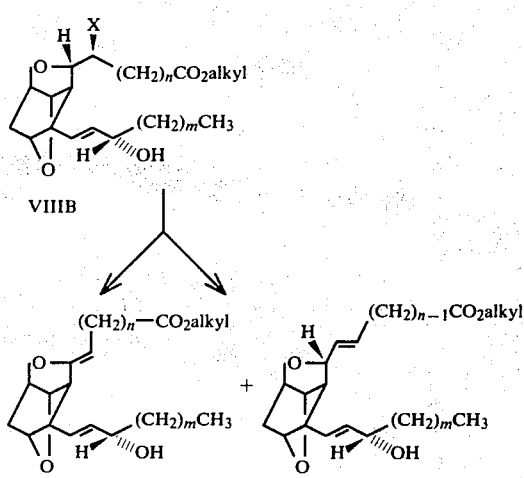

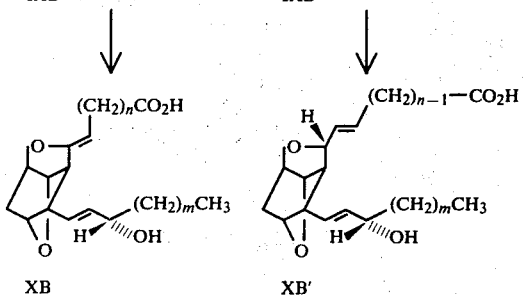

In carrying out the process as illustrated by the above reaction sequence (wherein Q in the compounds of the invention is a single bond), the aldehyde V (prepared as described in U.S. Pat. No. 4,187,236) in an inert solvent, such as tetrahydrofuran, is subjected to a Wittig reaction by treating same with a slurry of a carboxyalkyl triphenylphosphonium halide, such as 5-carboxypentyl triphenylphosphonium bromide (where n is 4) or 4-carboxybutyl triphenylphosphonium bromide (where n is 3), in dry tetrahydrofuran, the slurry also containing an alkali metal alkoxide, such as potassium t-butoxide, to obtain the hydroxy acid VI.

The acid-labile protecting group

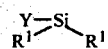

is removed from the hydroxy acid VI employing conventional procedures, such as by treatment with tetrabutyl ammonium fluoride in a solvent, such as tetrahydrofuran followed by neutralization; the residue is treated with a diazoalkane, such as diazomethane in an inert solvent like ether to form a mixture of isomers, that is, the dihydroxy esters VIIA and VIIB which are new intermediates

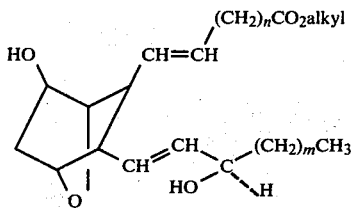

(hydroxy is β)

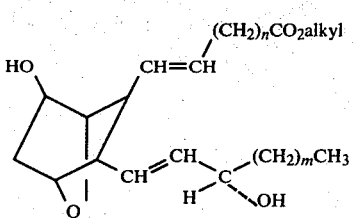

(hydroxy is α)

Where the hydroxy group in the side chain of the final product is to be β (compound XA), the dihydroxy ester VIIA is separated from its isomer VIIB by chromatography on silica and the dihydroxy ester VIIA in dichloromethane is treated with a halogen, such as iodine, fluorine or chlorine, and base, such as potassium bicarbonate to form the halo ether VIIIA which is a new intermediate

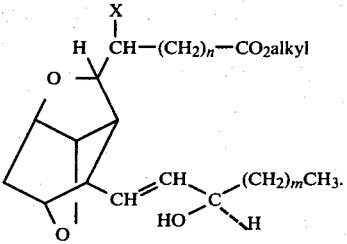

Treatment of the halo ether VIIIA in an inert solvent, such as toluene, with a base, such as diazabicyclo[5.4.0]undec-5-ene results in the formation of the enol ether IXA and the allylic ether IXA' which are new intermediates.

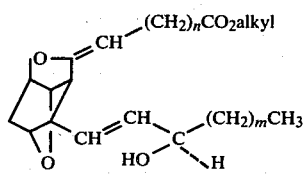

-continued

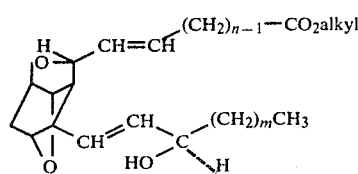 IXA'

The enol ether IXA and the allylic ether IXA' may be separated by chromatography on silica. The corresponding new free acids XA and XA' of the invention are obtained by treatment of each of the esters IXA and IXA' with a base, such as lithium hydroxide, followed by neutralization with an acid such as dilute hydrochloric acid.

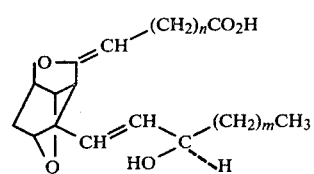 XA

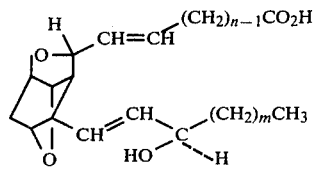 XA'

In a manner similar to that described above, starting with the new ester VIIB, the corresponding new (α) intermediates, namely, haloether VIIIB, enol ether IXB and allylic ether IXB', and the final free acids XB and XB' may be prepared.

Where Q in the compounds of the invention is —CH₂—, the following reaction sequence is applicable:

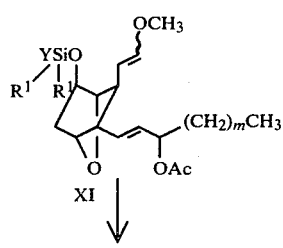 XI

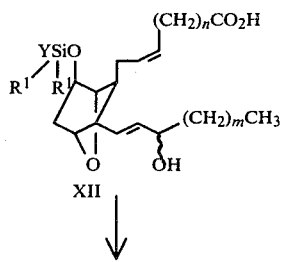 XII

-continued

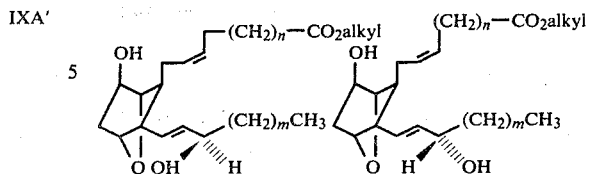
XIIIA    XIIIB

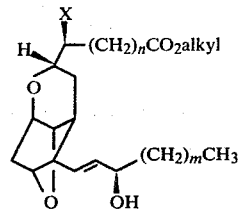 XIVA

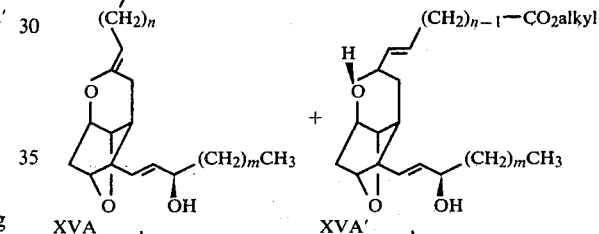
XVA    XVA'

-continued

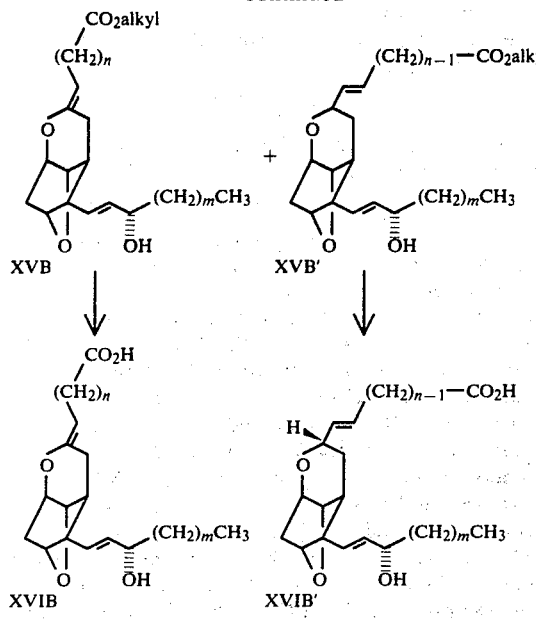

In carrying out the process as illustrated by the above reaction sequence (wherein Q in the compounds of the invention is —$CH_2$—), the enol ether XI (prepared as described in U.S. Pat. No. 4,187,236) in an inert solvent, such as tetrahydrofuran, is treated with an oxidizing agent such as mercuric acetate and then demetalated with a reducing agent like potassium iodide to yield the desired aldehyde, namely

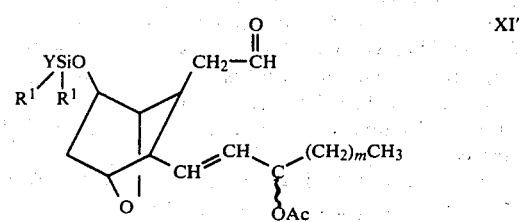

The aldehyde XI' is subjected to a Wittig reaction by treating same with a slurry of 5-carboxypentyl triphenylphosphonium bromide (where n is 4) or 4-carboxybutyl triphenylphosphonium bromide (where n is 3), in inert solvent, such as dry tetrahydrofuran, and alkali metal alkoxide, such as potassium t-butoxide, to obtain the hydroxy acid XII.

The acid-labile protecting group

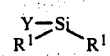

is removed from the hydroxy acid XII employing conventional procedures, such as by treatment with tetrabutyl ammonium fluoride in a solvent, such as tetrahydrofuran, followed by neutralization; the residue is treated with a diazoalkane, such as diazomethane in an inert solvent like ether to form a mixture of isomers, that is, the dihydroxy esters XIIIA and XIIIB which are new intermediates

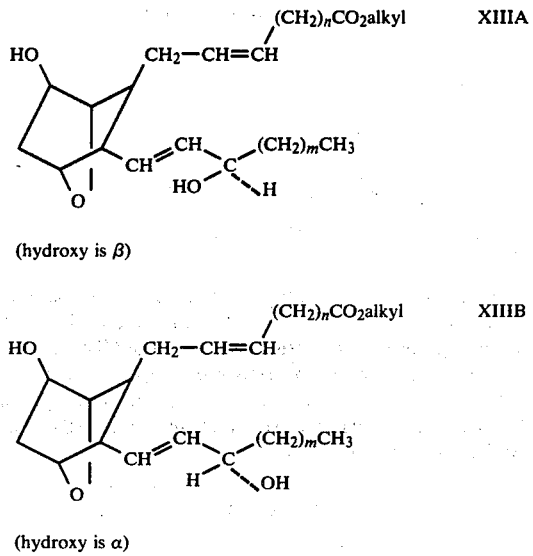

Where the hydroxy group in the side chain of the final product is to be β (compound XVIA), the dihydroxy ester XIIIA is separated from its isomer XIIIB by chromatography on silica and the dihydroxy ester XIIIA in dichloromethane is treated with a halogen, such as iodine, fluorine or chlorine, and base, such as potassium bicarbonate to form the halo ether XIVA which is a new intermediate

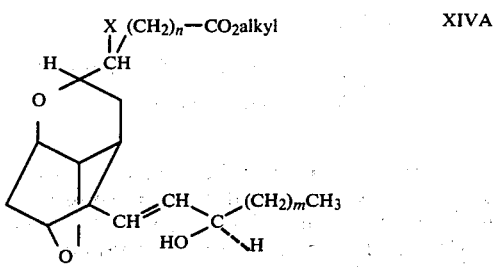

Treatment of the halo ether XIVA in inert solvent, such as toluene, with a base, such as diazabicyclo[5.4.-0]undec-5-ene results in the formation of the enol ether XVA and the allylic ether XVA' which are new intermediates.

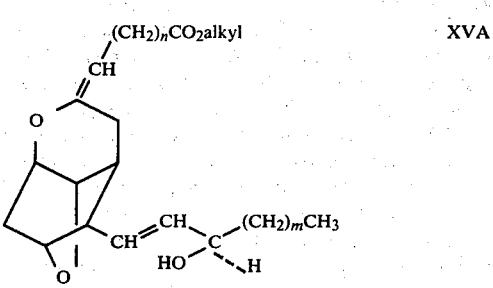

-continued

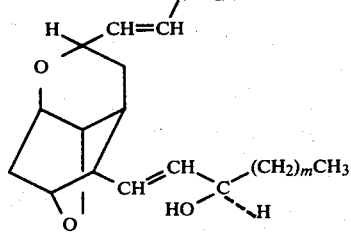
XVA'

The enol ether XVA and the allylic ether XVA' may be separated by chromatography on silica. The corresponding new free acids XVIA and XVIA' of the invention are obtained by treatment of each of the esters XVA and XVA' with a base, such as lithium hydroxide, followed by neutralization with an acid, such as dilute hydrochloric acid.

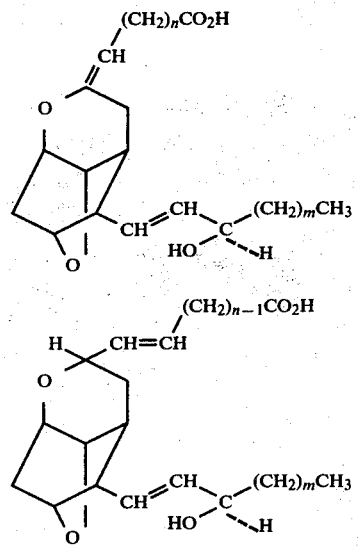

In a manner similar to that described above, starting with the new ester XIIIB, the corresponding new ($\alpha$) intermediates, namely, haloether XIVB, enol ether XVB and allylic ether XVB', and the final free acids XVIB and XVIB' may be prepared.

The compounds of this invention are cardiovascular agents useful as platelet aggregation inhibitors, e.g., for treatment of thrombolytic disease, such as coronary or cerebral thromboses. They are also selective thromboxane $A_2$ synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 gm/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of this invention.

EXAMPLE 1

[2$\alpha$,3a$\alpha$,5Z,7$\alpha$,7a$\alpha$,8S*(1E,3R)]-5-[Hexahydro-8-(3-hydroxy-1-octenyl)-2,7-methano-5H-furo[3,2-b]pyran-5-ylidene]pentanoic acid A. [1R-(1$\alpha$,2$\beta$,3$\beta$(5Z),4$\alpha$,5$\alpha$]-7-[2-(3-hydroxy-1-octenyl)-5-t-butyldimethylsilyloxy-7-oxabicyclo[2.2.1]hept-3-yl]-5-heptenoic acid A solution of [1R-(1$\alpha$,2$\beta$,3$\beta$,4$\alpha$,5$\alpha$)]-3-(2-methoxyethenyl)-5-t-butyl-dimethyl-silyloxy-7-oxabicyclo[2.2.1]heptane-2-methanol (0.006 mol) prepared as described in Example 1(f) of U.S. Pat. No. 4,187,236 in tetrahydrofuran/water (120:12) is chilled to 0° and treated with mercuric acetate (0.3 mol). The mixture is stirred at 0° or ninety minutes, then poured into 10% KI solution and stirred until the yellow color fades. The aqueous solution is extracted with benzene. The benzene phase is dried (MgSO$_4$) and concentrated to yield the desired aldehyde. A slurry of 4-carboxybutyltriphenylphosphonium bromide (0.037 mol) in dry tetrahydrofuran is treated with potassium t-butoxide (0.074 mol) and stirred at ambient temperature for 10 minutes to give an orange slurry. The above-described aldehyde in tetrahydrofuran is added to the orange slurry over 1 hour. The mixture is stirred at ambient temperature for an additional hour. The mixture is quenched with glacial acetic acid, and then poured into cold saturated ammonium chloride. The aqueous mixture is extracted with ether. The ether extract is washed with water, saturated NaCl and dried (MgSO$_4$). The solvent is evaporated to yield the title hydroxy acid.

B. [1S-(1$\alpha$,2$\alpha$(5Z),3$\beta$(1E,3R),4$\alpha$,6$\alpha$)]-7-[6-Hydroxy-3(3-hydroxy-1-octenyl)-7-oxabicyclo[2.2.1]hept-2-yl]-5-heptenoic acid, methyl ester and [1S-(1$\alpha$,2$\alpha$(5Z),-3$\beta$(1E,3S),4$\alpha$,6$\alpha$)]-7-[6-Hydroxy-3(3-hydroxy-1-octenyl)-7-oxabicyclo[2.2.1]hept-2-yl]-5-heptenoic acid, methyl ester A solution of the hydroxy acid from Example 1 part A (1 mmol), glacial acetic acid (0.04 mol) and tetrabutylammonium fluoride (0.01 mole) in tetrahydrofuran is heated at 50° for 3 days. The cooled reaction mixture is diluted with ether and washed with water, saturated NaCl and dried (MgSO$_4$). The solvent is evaporated to yield the dihydroxy acid (1$\alpha$,2$\alpha$(5Z),3$\beta$(1E),-4$\alpha$,6$\alpha$)-7-[6-hydroxy-3(3-hydroxy-1-octenyl)-7-oxabicyclo[2.2.1]hept-2-yl]-5-heptenoic acid. The dihydroxy acid (0.001 mole) in ether (50 ml) is treated with an ether solution of diazomethane and kept at room temperature for 15 minutes and the excess diazomethane is quenched with acetic acid. Evaporation of the solvents yields the title compounds which are purified by passage through a short column of silica gel. The title compounds are separated and [1S-(1$\alpha$,2$\alpha$(5Z),3$\beta$(-1E,3R),4$\alpha$,6$\alpha$)]-7-[6-hydroxy-3-(3-hydroxy-1-octenyl)-7-oxabicyclo[2.2.1]hept-2-yl]5-heptenoic acid, methyl ester is employed in the next step.

C. Iodoether Derived from [1S-(1$\alpha$,2$\alpha$(5Z),3$\beta$(1E,3R),4$\alpha$,6$\alpha$)]-7-[6-Hydroxy-3(3-hydroxy-1-octenyl)-7-oxabicyclo[2.2.1]hept-2-yl]-5-heptenoic acid, methyl ester To a solution of the methyl ester from Example 1, part B, in CH$_2$Cl$_2$ (18 ml) and saturated KHCO$_3$ (5 ml) at 0° is added I$_2$ (165 mg, 0.65 mmol). The reaction mixture is stirred at 0° for 2 hours, then quenched with saturated Na$_2$S$_2$O$_3$ solution, diluted with ether and layers are separated. The aqueous phase is reextracted, combined organic phases are washed with saturated NaCl and dried (MgSO$_4$). Solvent is evaporated to yield 230 mg (95%) of the title iodo ether.

D. [2α,3aα,5Z,7aα,8S(1E,3R)]-5-[Hexahydro-8-(3-hydroxy-1-octenyl)-2,7-methano-5H-furo[3,2-b]pyran-5-ylidene]pentanoic acid, methyl ester and [2α,3aα,5α(-E),-7α,7aα,8S*(1E,3R)]-5-[Hexahydro-8-(3-hydroxy-1-octenyl)-2,7-methano-2H-furo[3,2-b]pyran-5-yl]-4-pentenoic acid, methyl ester To a solution of the iodo ether from Example 1, part C (256 mg, 0.5 mmol) in toluene (10 ml) is added diazabicyclo[5.4.0]undec-5-ene (0.75 ml, 5 mmol). The resulting mixture is heated at 70° (bath temperature) for 20 hours. The cooled reaction mixture is poured into ether and pH 5 buffer. The resulting phases are separated, and the aqueous phase is reextracted. The combined organic phases are washed with pH 5 buffer, saturated KHCO$_3$, saturated NaCl and dried (MgSO$_4$). Solvent is evaporated to yield crude product as an oil which is chromatographed with ether-hexane (2:1) to yield the title compounds which are separated from each other by chromatography on silica.

E. [2α,3aα,5Z,7α,7aα,8S*(1E,3R)]-5-[Hexahydro-8-(3-hydroxy-1-octenyl)-2,7-methano-5H-furo[3,2-b]pyran-5-ylidene]pentanoic acid To an ice-cooled solution of [2α,3aα,5Z,-7α,7aα,8S(-1E,3R)]-5-[hexahydro-8-(3-hydroxy-1-octenyl)-2,7-methano-5H-furo[3,2-b]pyran-5-ylidene]pentanoic acid, methyl ester (from Part D) (132 mg, 0.35 mmol) in tetrahydrofuran (4.8 ml) is added 1 N LiOH (3.5 ml) dropwise. The resulting solution is stirred with continued cooling for 3½ hours, then diluted with ether and acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 2

[2α,3aα,5α(E),7α,7aα,8S*(1E,3R)]-5-[Hexahydro-8-(3-hydroxy-1-octenyl)-2,7-methano-2H-furo[3,2-b]pyran-5-yl]-4-pentenoic acid The mixture of esters prepared in Example 1 Part D are separated by chromatography on silica into the enol ether and allylic ether.

To an ice-cooled solution of [2α,3aα,5α(E),-7α,-7aα,8S*(1E,3R)]-5-[hexahydro-8-(3-hydroxy-1-octenyl)-2,7-methano-2H-furo[3,2-b]pyran-5-yl]-4-pentenoic acid, methyl ester (132 mg, 0.35 mmol) in tetrahydrofuran (4.8 ml) is added 1 N LiOH (3.5 ml) dropwise. The resulting solution is stirred with continued cooling for 3½ hours, then diluted with ether and acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 3

[2α,3aα,5Z,7α,7aα,8S*(1E,3S)]-5-[Hexahydro-8-(3-hydroxy-1-octenyl)-2,7-methano-5H-furo[3,2-b]pyran-5-ylidene]pentanoic acid A. Iodoether Derived from [1S-(1α,2α(5Z),-3β(1E,3S)4α,6α)]-7-[6-hydroxy-3(3-hydroxy-1-octenyl)-7-oxabicyclo[2.2.1]hept-2-y]5-heptenoic acid methyl ester To a solution of [1S-(1α,2α(5Z),3β(1E,3S)-4α,6α)]-7-[6-hydroxy-3(3-hydroxy-1-octenyl)-7-oxabicyclo[2.2.1-]hept-2-y]-5-heptenoic acid methyl ester (prepared in Example 1, part B), in CH$_2$Cl$_2$ (18 ml) and saturated KHCO$_3$ (5 ml) at 0° is added I$_2$ (165 mg, 0.65 mmol). The reaction mixture is stirred at 0° for 2 hours then quenched with saturated Na$_2$S$_2$O$_3$ solution, diluted with ether and layers are separated. The aqueous phase is reextracted, combined organic phases are washed with saturated NaCl and dried (MgSO$_4$). Solvent is evaporated to yield 230 mg (95%) of the title iodo ether.

B. [2α,3aα,5Z,7aα,8S(1E,3S)]-5-[Hexahydro-8-(3-hydroxy-1-octenyl)-2,7-methano-5H-furo[3,2-b]pyran-5-ylidene]pentanoic acid, methyl ester and [2α,3aα,5α(-E),-7α,7aα,8S*(1E,3S)]-5-[Hexahydro-8-(3-hydroxy-1-octenyl)-2,7-methano-2H-furo-[3,2-b]pyran-5-yl]-4-pentenoic acid, methyl ester To a solution of the iodo ether from part A above (256 mg, 0.5 mmol) in toluene (10 ml) is added diazabicyclo[5.4.0]undec-5-ene (0.75 ml, 5 mmol). The resulting mixture is heated at 70° (bath temperature) for 20 hours. The cooled reaction mixture is poured into ether and pH 5 buffer. The resulting phases are separated and the aqueous phase is reextracted. The combined organic phases are washed with pH 5 buffer, saturated KHCO$_3$, saturated NaCl and dried (MgSO$_4$). Solvent is evaporated to yield crude product as an oil which is chromatographed with ether-hexane (2:1) to yield the title compounds which are separated by chromatography on silica.

C. [2α,3aα,5Z,7α,7aα,8S*(1E,3S)]-5-[Hexa-hydro-8-(3-hydroxy-1-octenyl)-2,7-methano-5H-furo[3,2-b]pyran-5-ylidene]pentanoic acid To an ice-cooled solution of enol ether from Part B (132 mg, 0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentaneether and filtered through a bed of celite and Millipore filter to yield the title compound.

EXAMPLE 4

[2α,3aα,5α(E),7α,7aα,8S*(1E,3S)]-5-[Hexahydro-8-(3-hydroxy-1-octenyl)-2,7-methano-2H-furo[3,2-b]pyran-5-yl]-4-pentenoic acid The mixture of esters prepared in Example 3, part B, is separated by chromatography on silica gel into enol ether and allylic ether.

To an ice-cooled solution of allylic ether (132 mg, 0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 5

[2α,3aα,6Z,7aα,8S*(1E,3R)]-6-[Hexahydro-8-(3-hydroxy-1-octenyl)-2,7-methano-5H-furo[3,2-b]pyran-6-ylidine]hexanoic acid A. [1R-(1α,2β,3β(6Z),4α,5α)]-7-[2-hydroxymethyl-5-t-butyldimethylsilyloxy-7-oxabicyclo[2.2.1]hept-3-yl]-6-octenoic acid A solution of [1R-(1α,2β,3β,4α,5α)]-3-(2-methoxyethenyl)-5-t-butyl-dimethyl-silyloxy-7-oxabicyclo[2.2.1]heptane-2-methanol (0.006 mol) (prepared as described in U.S. Pat. No. 4,187,236) in tetrahydrofuran/water (120:12) is chilled to 0° and treated with mercuric acetate (0.3 mol). The mixture is stirred at 0° for 90 minutes then poured into 10% KI solution and stirred until the yellow color fades. The aqueous solution is extracted with benzene. The benzene phase is dried (MgSO$_4$) and concentrated to yield the desired aldehyde. A slurry of 4-carboxypentyltriphenylphosphonium bromide (0.037 mol) in dry tetrahydrofuran is treated with potassium t-butoxide (0.074 mol) and stirred at ambient temperature for 10 minutes to give an orange slurry. The above-described aldehyde in tetrahydrofuran is added to the orange slurry over 1 hour. The mixture is stirred at ambient temperature for an additional hour. The mixture is quenched with glacial acetic acid then poured into cold saturated ammonium chloride. The aqueous mixture is extracted with ether. The ether extract is washed with water, saturated NaCl and dried (MgSO$_4$). The solvent is evaporated to yield the title hydroxy acid.

B. (1α,2α(6Z), 3β(1E),4α,6α)-7-[6-Hydroxy-3(3-hydroxy-1-octenyl)-7-oxabicyclo[2.2.1]hept-2-yl]-6-octenoic acid, methyl ester A solution of the hydroxy acid from Part A (1 mmol), glacial acetic acid (0.04 mol) and tetrabutylammonium fluoride (0.01 mole) in tetrahydrofuran is heated at 50° for 3 days. The cooled reaction mixture is diluted with ether and washed with water, saturated NaCl and dried (MgSO$_4$). The solvent is evaporated to yield the dihydroxy acid ((1α,2α,(6Z), 3β(1E),4α,6α)-7-[6-hydroxy-3(3-hydroxy-1-octenyl)-7-oxabicyclo[2.2.1]hept-2-yl]-6-octenoic acid). The dihydroxy acid (0.001 mole) in ether (50 ml) is treated with an ether solution of diazomethane and kept at room temperature for 15 minutes and the excess diazomethane is quenched with acetic acid. Evaporation of the solvents yields the title compounds which are purified and separated by passage through a short column of silica gel. [1S-(1α,2α(6Z),3β(1E,3R)4α,6α)]-7-[6-Hydroxy-3(3-hydroxy-1-octenyl)-7-oxabicyclo[2.2.1]hept-2-yl]-6-octenoic acid, methyl ester is employed in the next step.

C. Iodoether Derived from [1S-(1α,2α,(6Z),3β(1E,3R)4α,6α)]-7-[6-Hydroxy-3(3-hydroxy-1-octenyl)-7-oxabicyclo[2.2.1]hept-2-yl]-6-octenoic acid, methyl ester To a solution of the methyl ester from Example 5, part B, in CH$_2$Cl$_2$ (18 ml) and saturated KHCO$_3$ (5 ml) at 0° is added I$_2$ (165 mg, 0.65 mmol). The reaction mixture is stirred at 0° for 2 hours, then quenched with saturated Na$_2$S$_2$O$_3$ solution, diluted with ether and layers are separated. The aqueous phase is reextracted, combined organic phases are washed with saturated NaCl and dried (MgSO$_4$). Solvent is evaporated to yield 230 mg (95%) of the title iodo ether.

D. [2α,3aα,6Z,7α,7aα,8S(1E,3R)]-5-[Hexahydro-8-(3-hydroxy-1-octenyl)-2,7-methano-5H-furo[3,2-b]pyran-5-ylidene]hexanoic acid, methyl ester and [2α,3aα,6α(E),7α,7aα,8S(1E,3R)]-5-[Hexahydro-8-(3-hydroxy-1-octenyl)-2,7-methano-2H-furo-[3,2-b]pyran-5-yl]-5-hexenoic acid, methyl ester To a solution of iodoether from Example 5, part C (256 mg, 0.5 mmol) in toluene (10 ml) is added diazobicyclo[5.4.0]undec-5-ene (0.75 ml, 5 mmol). The resulting mixture is heated at 70° (bath temperature) for 20 hours. The cooled reaction mixture is poured into ether and pH 5 buffer. The resulting phases are separated and the aqueous phase is reextracted. The combined organic phases are washed with pH 5 buffer, saturated KHCO$_3$, saturated NaCl and dried (MgSO$_4$). Solvent is evaporated to yield crude product as an oil which is chromatographed with ether-hexane (2:1) to yield the title compounds which are separated from each other by chromatography on silica.

E. [2α,3aα,6Z,7α,7aα,8S*(1E,3R)]-6-[Hexahydro-8-(3-hydroxy-1-octenyl)2,7-methano-5H-furo[3,2-b]pyran-6-ylidine]hexanoic acid To an ice-cooled solution of the enol ether from Part D (132 mg, 0.35 mmol) in tetrahydrofuran (4.8 ml) is added 1 N LiOH (3.5 ml) dropwise. The resulting solution is stirred with continued cooling for 3½ hours, then diluted with ether, and acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 6

[2α,3aα,5α(E),7α,7aα,8S*(1E,3R)]-6-[Hexahydro-8-(3-hydroxy-1-octenyl)-2,7-methano-2H-furo[3,2-b]-pyran-6-yl]-5-hexenoic acid The mixture of esters prepared in Example 5, Part D, is separated by chromatography into the two title compounds.

To an ice-cooled solution of allylic ether from Example 5 Part D (132 mg, 0.35 mmol) in tetrahydrofuran (4.8 ml) is added 1 N LiOH (3.5 ml) dropwise. The resulting solution is stirred with continued cooling for 3½ hours, then diluted with ether and acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 7

[2α,3aα,6Z,7α,7aα,8S*(1E,3S)]-6-[Hexahydro-8-(3-hydroxy-1-octenyl)-2,7-methano-5H-furo[3,2-b]pyran-6-ylidine]hexanoic acid A. Iodoether derived from the methyl ester of (1α,2α(6Z),3β(1E,3S),4α,6α)-7-[6-hydroxy-3(3-hydroxy-1-octenyl)-7-oxabicyclo[2.2.1]hept-2-yl]-6-octenoic acid To a solution of the methyl ester of (1α,2α(6Z),3β(1E,3S),4α,6α)-7-[6-hydroxy-3(3-hydroxy-1-octenyl)-7-oxabicyclo[2.2.1]hept-2-yl]6-octenoic acid prepared in Example 5, Part B, in CH$_2$Cl$_2$ (18 ml) and saturated KHCO$_3$ (5 ml) at 0° is added I$_2$ (165 mg, 0.65 mmol). The reaction mixture is stirred at 0° for 2 hours then quenched with saturated Na₂S₂O₃ solution, diluted with ether and layers are separated. The aqueous phase is reextracted, combined organic phases are washed with saturated NaCl and dried (MgSO₄). Solvent is evaporated to yield 230 mg (95%) of the title iodo ether.

B. [2α,3aα,6Z,7α,7aα,8S(1E,3S)]-5-[Hexahydro-8-(3-hydroxy-1-octenyl)-2,7-methano-5H-furo[3,2-b]pyran-5-ylidene]hexanoic acid, methyl ester and [2α,3aα,6α(E),7α,7aα,8S(1E,3S)]-5-[Hexahydro-8-(3-hydroxy-1-octenyl)-2,7-methano-2H-furo-[3,2-b]pyran-5-yl]-5-hexenoic acid, methyl ester To a solution of iodo ether from Part A above (256 mg, 0.5 mmol) in toluene (10 ml) is added diazobicyclo[5.4.0]undec-5-ene (0.75 ml, 5 mmol). The resulting mixture is heated at 70° (bath temperature) for 20 hours. The cooled reaction mixture is poured into ether and pH 5 buffer. The resulting phases are separated and the aqueous phase is reextracted. The combined organic phases are washed with pH 5 buffer, saturated KHCO₃, saturated NaCl and dried (MgSO₄). Solvent is evaporated to yield crude product as an oil which is chromatographed with ether-hexane (2:1) to yield the title compounds which are separated by chromatography on silica.

C. [2α,3aα,6Z,7α,7aα,8S*(1E,3S)]-6-[Hexahydro-8-(3-hydroxy-1-octenyl)-2,7-methano-5H-furo[3,2-b]pyran-6-ylidine]hexanoic acid To an ice-cooled solution of the enol ether (132 mg, 0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO₄). Solvent is evaporated to yield acid as an oil which is taken up in pentane-ether and filtered through a bed of celite and Millipore filter to yield the title compound.

EXAMPLE 8

[2α,3aα,5α(E),7α,7aα,8S*(1E,3S)]-6-[Hexahydro-8-(3-hydroxy-1-octenyl)-2,7-methano-2H-furo[3,2-b]pyra-6-yl]-5-hexenoic acid The mixture of esters prepared in Example 7, Part B, is separated by chromatography into allylic ether and enol ether.

To an ice-cooled solution of the allylic ether (132 mg, 0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO₄). Solvent is evaporated to yield acid as an oil which is taken up in pentane-ether and filtered through a bed of celite and Millipore filter to yield the title compound.

EXAMPLE 9

[2α,3aα,6Z,6α,6aα,7S*(1E,3R)]-6-[Tetrahydro-7-(3-hydroxy-1-octenyl)-2,6-methano-furo[3,2-b]furan-5(2H)-ylidene]hexanoic acid A. [1R-(1α,2β,3β(6Z)-4α,5α)]-7-[2(3-Hydroxy-1-octenyl)-5-t-butyldimethylsilyloxy-7-oxabicyclo[2.2.1]hept-3-yl]-6 heptenoic acid A slurry of 5-carboxypentyltriphenylphosphonium bromide (16.4 g, 0.037 mol) in dry tetrahydrofuran (180 ml) is treated with potassium t-butoxide (8.28 g, 0.074 mol) and stirred at ambient temperature for 10 minutes to form an orange colored slurry. The aldehyde [1R-(1α,2β,3β(E),4α,5α)]-2(3-acetoxy-1-octenyl)-3-formyl-5-t-butyldimethylsilyloxy-7-oxabicyclo[2.2.1]heptane (0.006 mol), prepared as described in U.S. Pat. No. 4,187,236, is dissolved in 50 ml of dry tetrahydrofuran and added to the above orange slurry over one hour. The mixture is stirred at room temperature for one additional hour, quenched with glacial acetic acid, then poured into cold saturated NH₄Cl solution. The aqueous mixture is extracted with ether and combined ether extracts are washed with water, saturated NaCl and dried (MgSO₄). Solvent is evaporated and the residue is chromatographed to give the title compound as a mixture of allylic alcohol epimers.

B. [1R-(1α,2β,3β(6Z),4α,5α)]-7-[2(3-Hydroxy-1-octenyl)-5-t-butyldimethylsilyloxy-7-oxabicyclo[2.2.1]hept-3-yl]-6 heptenoic acid, methyl ester A solution of the above alcohol (0.001 mol), glacial acetic acid (2.4 g, 0.04 mol) and tetrabutylammonium fluoride (3.15 g, 0.01 mol) in tetrahydrofuran (10 ml) is heated at 50° for 3 days. The cooled reaction mixture is diluted with ether, washed with water until the aqueous layer is neutral, then with saturated NaCl. The ether solution is dried (MgSO₄) and concentrated. The residue is treated with diazomethane to yield [1R-(1α,2β(6Z),3α(1E),4α,5α)]-7-[2(3-hydroxy-1-octenyl)-5-hydroxy-7-oxabicyclo[2.2.1]hept-3-yl]6-heptaoic acid, methyl ester as a mixture of allylic alcohol epimers which are separated by chromatography on silica.

C. Iodoether derived from [1R-(1α,2β(6Z),3α(-1E,3R),4α,5α)]-7-[3(3-hydroxy-1-octenyl)6-hydroxy-7-oxabicyclo[2.2.1]hept-2-yl]6-heptenoic acid, methyl ester The dihydroxy ester ([1R-(1α,2β(6Z),3α-(1E,3R),4α,5α)]-7-[3(3-hydroxy-1-octenyl)-6-hydroxy-7-oxabicyclo[2.2.1]hept-2-yl]-6-heptenoic acid, methyl ester) in CH₂Cl₂ solution is treated with 1.1 equivalent of I₂ and saturated KHCO₃ at 0° for 2 hours. The excess I₂ is then quenched with saturated Na₂S₂O₃ solution and the mixture is diluted with ether. The ether phase is washed with saturated NaCl and dried (MgSO₄). The solvent is evaporated to yield the title iodoether.

D. [2α,3aα,6Z,6α,6aα,7S*(1E,3R)]-6-[Tetrahydro-7-(3-hydroxy-1-octenyl)2,6-methano-furo[3,2-b]furan-5(2H)ylidene]hexanoic acid, methyl ester and [2α,3aα,5α(E),6α,6aα,7S*(1E,3R)]-6-[Hexahydro-7-(3-hydroxy-1-octenyl)-2,6-methano-furo[3,2-b]furan-5-yl]-5-hexenoic acid, methyl ester To a solution of the iodoether from Part B (0.5 mmol) in toluene (10 ml) is added diazabicyclo[5.4.0]undec-5-ene (5 mmol). The reaction mixture is heated at 70° for 20 hours. The cooled reaction mixture is poured into ether and pH 5 buffer. The organic phase is washed with saturated KHCO₃, saturated NaCl and dried (MgSO₄). Solvent is evaporated to yield the enol ether and allylic ether named above which are separated by chromatography on silica.

E. [2α,3aα,6Z,6α,6aα,7S*(1E,3R)]-6-[Tetra-hydro-7-(3-hydroxy-1-octenyl)-2,6-methano-furo[3,2-b]furan-5(2H)-ylidene]hexanoic acid To an ice-cooled solution of enol ether (from Part D) (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 10

[2α,3aα,5α(E),6α,6aα,7S*(1E,3R)]-6-[Hexahydro-7-(3-hydroxy-1-octenyl)-2,6-methano-furo[3,2-b]furan-5-yl]-5-hexenoic acid To an ice-cooled solution of allylic ether (from Example 9, Part D) (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 11

[2α,3aα,6Z,6α,6aα,7S*(1E,3S)]-6-[Tetrahydro-7-(3-hydroxy-1-octenyl)-2,6-methano-furo[3,2-b]furan-5(2H)-ylidene]hexanoic acid A. Iodoether Derived from [1R(1α,2β, 16Z),3α-(1E,3S)4α,5α]-7-[3(3-hydroxy-1-octenyl)-6-hydroxy-7-oxabicyclo[2.2.1]hept-2-yl]-6-heptenoic acid, methyl ester The dihydroxy ester [1R-(1α,2β(6Z),3α(1E,3S),-4α,-5α)]-7-[3(3-hydroxy-1-octenyl)-6-hydroxy-7-oxabicyclo[2.2.1]hept-2-yl]-6-heptenoic acid, methyl ester, prepared in Example 9, Part B, in CH$_2$Cl$_2$ solution is treated with 1.1 equivalent of I$_2$ and saturated KHCO$_3$ at 0° for 2 hours. The excess I$_2$ is then quenched with saturated Na$_2$S$_2$O$_3$ solution and the mixture is diluted with ether. The ether phase is washed with saturated NaCl and dried (MgSO$_4$). The solvent is evaporated to yield the title iodoether.

B. [2α,3aα,6Z,6α,6aα,7S*(1E,3S)]-6-[Tetrahydro-7-(3-hydroxy-1-octenyl)-2,6-methano-furo[3,2-b]furan-5(2H)-ylidene]hexanoic acid, methyl ester and [2α,3aα,-5α(E),6α,6aα,7S*(1E,3S)]-6-[Hexahydro-7-(3-hydroxy-1-octenyl)-2,6-methano-furo[3,2-b]furan-5-yl]-5-hexenoic acid, methyl ester To a solution of the iodoether from Part A above (0.5 mmol) in toluene (10 ml) is added diazabicyclo[5.4.0]undec-5-ene (5 mmol). The reaction mixture is heated at 70° for 20 hours. The cooled reaction mixture is poured into ether and pH 5 buffer. The organic phase is washed with saturated KHCO$_3$, saturated NaCl and dried (MgSO$_4$). Solvent is evaporated to yield enol ether and allylic ether named above which are separated by chromatography on silica.

C. [2α,3aα,6Z,6α,6aα,7S*(1E,3S)]-6-[Tetrahydro-7-(3-hydroxy-1-octenyl)-2,6-methano-furo[3,2-b]furan-5(2H)-ylidene]hexanoic acid To an ice-cooled solution of enol ether from Part B (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 12

[2α,3aα,5α(E),6α,6aα,7S*(1E,3S)]-6-[Hexahydro-7-(3-hydroxy-1-octenyl)-2,6-methano-furo[3,2-b]furan-5-yl]-5-hexenoic acid To an ice-cooled solution of the allylic ether from Example 11, part B, (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution of pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 13

[2α,3aα,5Z,6α,6aα,7S*(1E,3R)]-5-[Tetrahydro-7-(3-hydroxy-1-octenyl)-2,6-methano-furo[3,2-b]furan-5(2H)-ylidene]pentanoic acid A. [1R-(1α,2β,3α,(5Z),4α,5α)]-7-[2(3-hydroxy-1-octenyl)-5-t-butyldimethylsilyloxy-7-oxabicyclo[2.2.1]hept-3-yl]-5-pentenoic acid, methyl ester A slurry of 5-carboxybutyltriphenyl phosphonium bromide (16.4 g, 0.037 mol) in dry tetrahydrofuran (180 ml) is treated with potassium t-butoxide (8.28 g, 0.074 mol) and stirred at ambient temperature for 10 minutes. The aldehyde [1R-(1α,2β,3β(E),4α,5α)]-2(3-acetoxy-1-octenyl)-3-formyl-5-t-butyldimethylsilyloxy-7-oxabicyclo[2.2.1]heptane (0.006 mol) (prepared as described in U.S. Pat. No. 4,187,236) is dissolved in 50 ml of dry tetrahydrofuran and added to the above slurry over one hour. The mixture is stirred at room temperature for one additional hour, quenched with glacial acetic acid, then poured into cold saturated NH$_4$Cl solution. The aqueous mixture is extracted with ether and combined ether extracts are washed with water, saturated NaCl and dried (MgSO$_4$). Solvent is evaporated and the residue is chromatographed to give the alcohol acids. A solution of the above alcohol (0.001 mol), glacial acetic acid (2.4 g, 0.04 mol) and tetrabutylammonium fluoride (3.15 g, 0.01 mol) in tetrahydrofuran (10 ml) is heated at 50° for 3 days. The cooled reaction mixture is diluted with ether, washed with water until the aqueous layer is neutral, then with saturated NaCl. The ether solution is dried (MgSO$_4$) and concentrated. The residue is treated with diazomethane to yield title compound as a mixture of allylic alcohol epimers which are separated by chromatography on silica.

B. Iodoether Derived From [1R-(1α,2β(1E,3R),-3α(5Z),4α,5α)]-7-[2(3-hydroxy-1-octenyl)-5-hydroxy-7-oxabicyclo[2.2.1]hept-3-yl]-5-pentenoic acid, methyl ester The dihydroxy ester [1R-(1α,2β(1E,3R),3α(5Z),-4α,-5α)]-7-[2(3-hydroxy-1-octenyl)-5-hydroxy-7-oxabicyclo[2.2.1]hept-3-yl]-5-pentenoic acid, methyl ester in CH$_2$Cl$_2$ solution is treated with 1.1 equivalents of I$_2$ and saturated KHCO$_3$ at 0° for 2 hours. The excess I$_2$ is then quenched with saturated Na$_2$S$_2$O$_3$ solution and the mixture is diluted with ether. The ether phase is washed with saturated NaCl and dried (MgSO$_4$). The solvent is evaporated to yield the title iodoether.

C. [2α,3aα,5Z,6α,6aα,7S*(1E,3R)]-6-[Tetrahydro-7-(3-hydroxy-1-octenyl)-2,6-methano-furo[3,2-b]furan-5(2H)-ylidene]-pentanoic acid, methyl ester and [2α,-3aα,5α(E),6α,6aα,7S*(1E,3R)]-6-[Hexahydro-7-(3- hydroxy-1-octenyl)-2,6-methano-furo[3,2-b]furan-5-yl]-4-pentenoic acid, methyl ester To a solution of iodoether from Part B (0.5 mmol) in toluene (10 ml) is added diazabicyclo[5.4.0]undec-5-ene (5 mmol). The reaction mixture is heated at 70° for 20 hours. The cooled reaction mixture is poured into ether and pH 5 buffer. The organic phase is washed with saturated KHCO$_3$, saturated NaCl and dried (MgSO$_4$). Solvent is evaporated to yield the enol ether [2α,3aα,5Z,6α,-6aα,7S*(1E,3R)]-6-[tetrahydro-7-(3-hydroxy-1-octenyl)-2,6-methano-furo[3,2-b]furan-5(2H)-ylidene]pentanoic acid, methyl ester and allylic ether [2α,3aα,5α(E),6α,6aα,7S*(1E,3R)]-6-[hexahydro-7-(3-hydroxy-1-octenyl)-2,6-methano-furo[3,2-b]furan-5-yl]-4-pentenoic acid, methyl ester which are separated by chromatography on silica.

D. [2α,3aα,5Z,6α,6aα,7S*(1E,3R)]-5-[Tetrahydro-7-(3-hydroxy-1-octenyl)-2,6-methano-furo[3,2-b]furan-5(2H)ylidene]pentanoic acid To an ice-cooled solution of enol ether (from Part C) (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 14

[2α,3aα,5α(E),6α,6aα,7S*(1E,3R)]-5-[Hexahydro-7-(3-hydroxy-1-octenyl)-2,6-methano-furo[3,2-b]furan-5-yl]-4-pentenoic acid To an ice-cooled solution of allylic ether from Part C, Example 13, (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 15

[2α,3aα,5Z,6α,6aα,7S*(1E,3S)]-5-[Tetrahydro-7-(3-hydroxy-1-octenyl)-2,6-methano-furo[3,2-b]furan-5(2H)-ylidine]pentanoic acid A. Iodoether of [1R(1α,2β(1E,3S),3α(5Z),-4α,5α]-7-[2(3-hydroxy-1-octenyl)-5-hydroxy-7-oxabicyclo[2.2.1]hept-3-yl]-5-pentenoic acid, methyl ester The dihydroxy ester [1R,(1α,2β(1E,3S),3α(5Z),-4α,-5α)]-7-[2(3-hydroxy-1-octenyl)-5-hydroxy-7-oxabicyclo[2.2.1]hept-3-yl]-5-pentenoic acid, methyl ester prepared in Example 13, Part A, in CH$_2$Cl$_2$ is treated with 1.1 equivalent of I$_2$ and saturated KHCO$_3$ at 0° for 2 hours. The excess I$_2$ is then quenched with saturated Na$_2$S$_2$O$_3$ solution and the mixture is diluted with ether. The ether phase is washed with saturated NaCl and dried (MgSO$_4$). The solvent is evaporated to yield the title iodoether.

B. [2α,3aα,5Z,6α,6aα,7S*(1E,3S)]-6-[Tetra-hydro-7-(3-hydroxy-1-octenyl)-2,6-methano-furo[3,2-b]furan-5(2H)-ylidene]pentanoic acid, methyl ester and [2α,-3aα,5α(E),6α,6aα,7S*(1E,3S)]-6-[Hexahydro-7-(3-hydroxy-1-octenyl)-2,6-methano-furo[3,2-b]furan-5-yl]-4-pentenoic acid, methyl ester To a solution of the iodoether from Part A (0.5 mmol) in toluene (10 ml) is added diazabicyclo[5.4.0]undec-5-ene (5 mmol). The reaction mixture is heated at 70° for 20 hours. The cooled reaction mixture is poured into ether and pH 5 buffer. The organic phase is washed with saturated KHCO$_3$, saturated NaCl and dried (MgSO$_4$). Solvent is evaporated to yield enol ether [2α,3aα,5Z,6α,6aα,7S*(1E,3S)]-6-[tetrahydro-7-(3-hydroxy-1-octenyl)-2,6-methano-furo[3,2-b]furan-5(2H)-ylidene]pentanoic acid, methyl ester and allylic ether [2α,3aα,5α(E),-6α,6aα,7S*(1E,3S)]-6-[hexahydro-7-(3-hydroxy-1-octenyl)-2,6-methano-furo[3,2-b]furan-5-yl]-4-pentenoic acid, methyl ester which are separated by chromatography on silica.

C. [2α,3aα,5Z,6α,6aα,7S*(1E,3S)]-5-[Tetrahydro-7-(3-hydroxy-1-octenyl)-2,6-methano-furo[3,2-b]furan-5(2H)ylidene]pentanoic acid To an ice-cooled solution of enol ether from Part B (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

EXAMPLE 16

[2α,3aα,5α(E),6α,7aα,7S*(1E,3S)]-5-[Hexahydro-7-(3-hydroxy-1-octenyl)-2,6-methano-furo[3,2,-b]-furan-5-yl]-4-pentenoic acid To an ice-cooled solution of allylic ether from Example 15, Part B, (0.35 mmol) in tetrahydrofuran (4.8 ml) is added 1 N LiOH (3.5 ml) dropwise. The resulting solution is stirred with continued cooling for 3½ hours, then diluted with ether, acidified with saturated oxalic acid solution to pH 3. The ether phase is washed with water, saturated NaCl and dried (MgSO$_4$). Solvent is evaporated to yield acid as an oil which is taken up in pentane-ether and filtered through a bed of celite and Millipore filter to yield the title compound.

What is claimed is:

1. A compound having the structural formula

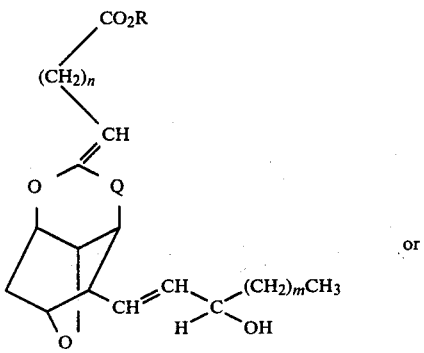

or

-continued

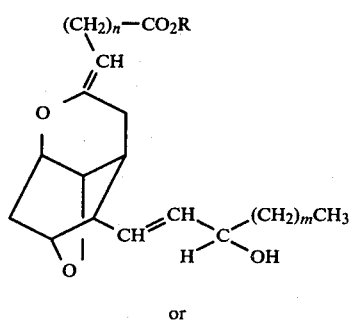

and including all stereoisomers thereof, wherein R is hydrogen or lower alkyl, Q is a single bond or —CH$_2$—, m is 1 to 9, and n is 3 or 4.

2. The compound of claim 1 having the structure

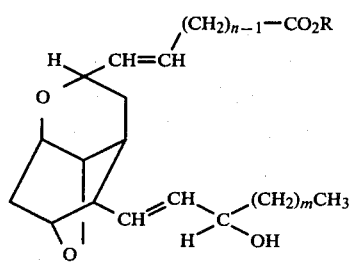

or

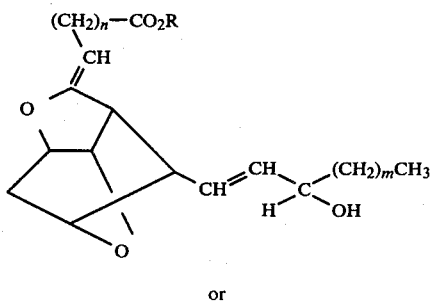

and including all stereoisomers thereof.

3. The compound of claim 1 having the structure

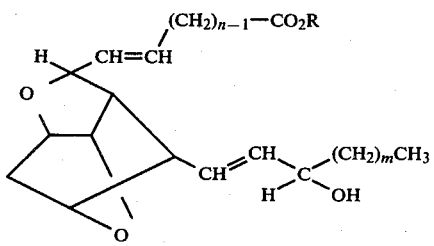

and including all stereoisomers thereof.

4. The compound of claim 1 wherein R is hydrogen and m is 4 so that (CH$_2$)$_m$CH$_3$ represents C$_5$H$_{11}$.

5. The compound of claim 2 having the structure

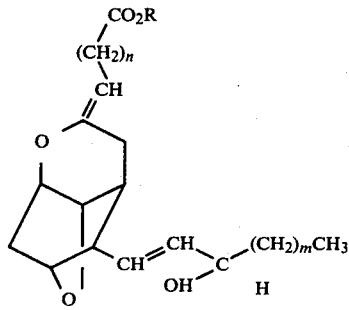

or

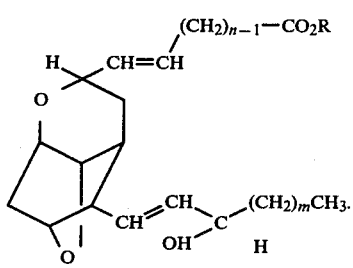

6. The compound of claim 5 wherein R is H and —(CH$_2$)$_m$CH$_3$ is —C$_5$H$_{11}$.

7. The compound of claim 6 wherein n is 3 and having the name [2α,3aα,5Z,7α,7aα,8S*(1E,3R)]-5-[hexahydro-8-(3-hydroxy-1-octenyl)-2,7-methano-5H-furo[3,2-b]pyran-5-ylidene]pentanoic acid or [2α,3aα,5α(E),7α,7aα,8S*(1E,3R)]-5-[hexahydro-8-(3-hydroxy-1-octenyl)-2,7-methano-2H-furo[3,2-b]pyran-5-yl]-4-pentenoic acid.

8. The compound of claim 6 wherein n is 4 and having the name [2α,3aα,6Z,7α,7aα,8S*(1E,3R)]-6-[hexahydro-8-(3-hydroxy-1-octenyl)-2,7-methano-5H-furo[3,2-b]pyran-6-ylidine]hexanoic acid or [2α,3aα,5α(E),7α,7aα,8S*(1E,3R)]-6-[hexahydro-8-(3-hydroxy-1-octenyl)-2,7-methano-2H-furo[3,2-b]pyran-6-yl]-5-hexenoic acid.

9. The compound of claim 2 having the structure

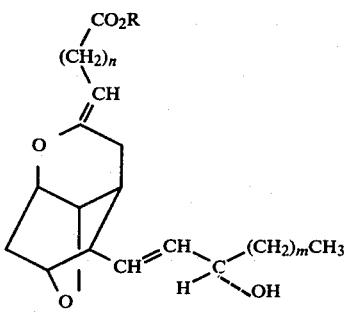

or

-continued

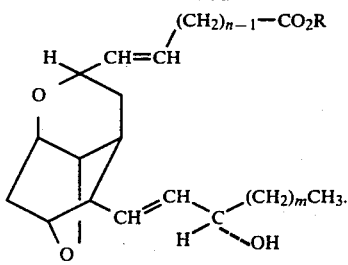

10. The compound of claim 9 wherein R is H and —(CH₂)ₘCH is —C₅H₁₁.

11. The compound of claim 10 wherein n is 3 and having the name [2α,3aα,5Z,7α,7aα,8S*(1E,3S)]-5-[hexahydro-8-(3-hydroxy-1-octenyl)-2,7-methano-5H-furo[3,2-b]pyran-5-ylidene]pentanoic acid or [2α,3aα,-5α(E),7α,7aα,8S*(1E,3S)]-5-[hexahydro-8-(3-hydroxy-1-octenyl)-2,7-methano-2H-furo[3,2-b]-pyran-5-yl]-4-pentenoic acid.

12. The compound of claim 10 wherein n is 4 and having the name [2α,3aα,6Z,7α,7aα,8S*(1E,3S)]-6-[hexahydro-8-(3-hydroxy-1-octenyl)-2,7-methano-5H-furo[3,2-]pyran-6-ylidine]hexanoic acid or [2α,3aα,-5α(E),7α,7aα,8S*(1E,3S)]-6-[hexahydro-8-(3-hydroxy-1-octenyl)-2,7-methano-2H-furo-[3,2-b]pyran-6-yl]-5-hexenoic acid.

13. The compound of claim 3 having the structure

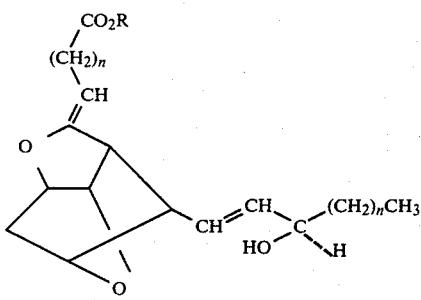

or

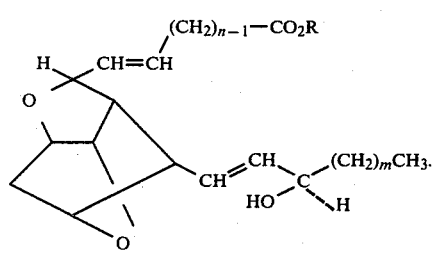

14. The compound of claim 13 wherein R is H and —(CH₂)ₘCH₃ is C₅H₁₁.

15. The compound of claim 14 wherein n is 3 and having the name [2α,3aα,6Z,6α,6aα,7S*(1E,3R)]-6-[tetrahydro-7-(3-hydroxy-1-octenyl)-2,6-methano-furo[3,2-b]furan-5(2H)-ylidene]hexanoic acid or [2α,3aα,5α(E),-6α,6aα,7S*(1E,3R)]-6-[hexahydro-7-(3-hydroxy-1-octenyl)-2,6-methano-furo[3,2-b]-furan-5-yl]-5-hexanoic acid.

16. The compound of claim 14 wherein n is 4 and having the name [2α,3aα,5Z,6α,6aα,7S*(1E,3R)]-5-[tetrahydro-7-(3-hydroxy-1-octenyl)-2,6-methano-furo[3,2-b]furan-5(2H)-ylidene]pentanoic acid or [2α,3aα,-5α(E),6α,6aα,7S*(1E,3R)]-5-[hexahydro-7-(3-hydroxy-1-octenyl)-2,6-methano-furo[3,2-b]-furan-5-yl]-4-pentenoic acid.

17. The compound of claim 13 having the structure

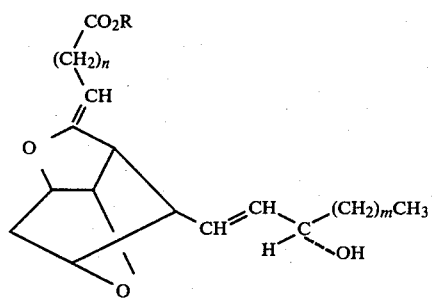

or

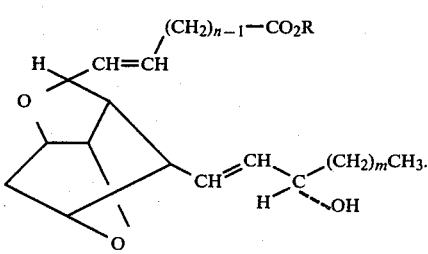

18. The compound of claim 17 wherein R is H and —(CH₂)ₘCH₃ is —C₅H₁₁.

19. The compound of claim 18 wherein n is 3 and having the name [2α,3aα,5Z,6α,6aα,7S*(1E,3S)]-5-[tetrahydro-7-(3-hydroxy-1-octenyl)-2,6-methano-furo[3,2-b]furan-5(2H)-ylidine]pentanoic acid or [2α,3aα,5α(E),-6α,7aα,7S*(1E,3S)]-5-[hexahydro-7-(3-hydroxy-1-octenyl)-2,6-methano-furo[3,2-b]furan-5-yl]-4-pentenoic acid.

20. The compound of claim 18 wherein n is 4 and having the name [2α,3aα,6Z,6α,6aα,7S*(1E,3S)]-6-[tetrahydro-7-(3-hydroxy-1-octenyl)-2,6-methano-furo[3,2-b]furan-5(2H)-ylidene]hexanoic acid or [2α,3aα,5α(E),-6α,6aα,7S*(1E,3S)]-6-[hexahydro-7-(3-hydroxy-1-octenyl)-2,6-methano-furo[3,2-b]furan-5-yl]-5-hexenoic acid.

21. The compound of claim 1 wherein R is lower alkyl.

22. The compound of claim 21 wherein R is CH₃ and (CH₂)ₘCH₃ is C₅H₁₁.

23. The compound of claim 2 wherein R is CH₃ and (CH₂)ₘCH₃ is C₅H₁₁.

24. The compound of claim 3 wherein R is CH₃ and (CH₂)ₘCH₃ is C₅H₁₁.

* * * * *

UNITED STATES PATENT AND TRADEMARK OFFICE
CERTIFICATE OF CORRECTION

PATENT NO. : 4,360,685
DATED : November 23, 1982
INVENTOR(S) : Martin F. Haslanger et al.

It is certified that error appears in the above—identified patent and that said Letters Patent is hereby corrected as shown below:

Column 15, line 6, after "6Z" insert --7α,--.
Column 15, line 58, "fron" should read --from--.
Column 17, line 13, "diazobicy" should read --diazabicy--.
Column 18, line 29, "heptaoic" should read --heptenoic--.
Column 24, Claim 5, in the first structure, in the lower side chain please change "[structure]" to read --[structure]-- and in the second structure, in the lower side chain please change "[structure]" to read --[structure]--.
Column 25, line 14, "$-(CH_2)_m CH$" should read -- $-(CH_2)_m CH_3$ --.

Signed and Sealed this

Fifteenth Day of February 1983

[SEAL]

Attest:

GERALD J. MOSSINGHOFF

*Attesting Officer*      *Commissioner of Patents and Trademarks*